United States Patent [19]

Schelhas

[11] Patent Number: 4,919,674
[45] Date of Patent: Apr. 24, 1990

[54] HIP CUP FOR A HIP JOINT ACETABULAR PROSTHESIS

[75] Inventor: Klaus-Dieter Schelhas, Bremen, Fed. Rep. of Germany

[73] Assignee: Orthoplant Endioprothetick GmbH, Bremen, Fed. Rep. of Germany

[21] Appl. No.: 145,289

[22] Filed: Jan. 19, 1988

[30] Foreign Application Priority Data

Jan. 20, 1987 [DE] Fed. Rep. of Germany ....... 3701381

[51] Int. Cl.$^5$ .............................................. A61F 2/34
[52] U.S. Cl. .................................................. 623/22
[58] Field of Search ........................ 623/16, 18, 19, 20, 623/22, 23; 128/1 R, 92 YZ; 403/122, 125, 135

[56] References Cited

U.S. PATENT DOCUMENTS

| | | | |
|---|---|---|---|
| 3,813,699 | 6/1974 | Giliberty | 623/22 |
| 3,818,512 | 6/1974 | Shersher | 623/23 |
| 4,231,673 | 11/1980 | Saton et al. | 403/125 |

FOREIGN PATENT DOCUMENTS

| | | | |
|---|---|---|---|
| 2932744 | 2/1980 | Fed. Rep. of Germany | 623/22 |
| 8302555 | 8/1983 | World Int. Prop. O. | 623/22 |

Primary Examiner—David J. Isabella
Attorney, Agent, or Firm—Merchant, Gould, Smith, Edell, Welter & Schmidt

[57] ABSTRACT

Presented is a hip cup for a hip joint acetabular prosthesis that includes a metallic outer cup and a cup body made of plastic inside the outer cup. To guarantee a movement- and deformation-free attachment of the cup body, the cup body is enclosed in tightly fitting fashion, toward the outer cup, by a metallic jacket, and the insert formed of cup body and jacket can be anchored in the outer cup in tightly fitting fashion with at least one attaching element.

10 Claims, 2 Drawing Sheets

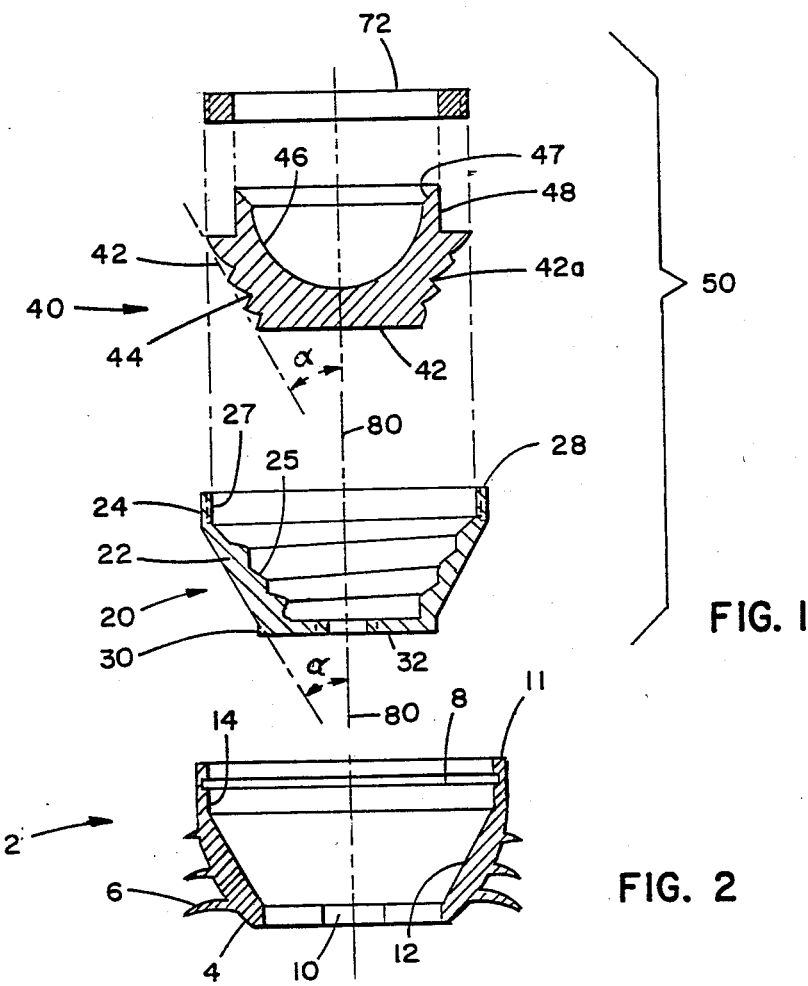
FIG. 1
FIG. 2
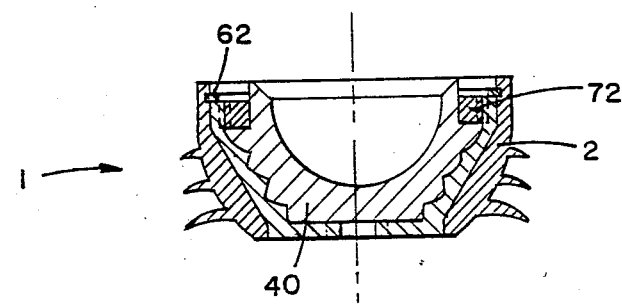
FIG. 3

HIP CUP FOR A HIP JOINT ACETABULAR PROSTHESIS

DESCRIPTION

The object of the invention is a hip cup for a hip joint acetabular prosthesis with a metallic outer cup, and with a cup body made of plastic in the outer cup having on the face side an exposed cup surface, and in the outer cup a circular supporting surface, with the inner form of the outer cup and the supporting surface of the cup body tapering toward the crown, along with a method for its production.

A hip cup of this type is known, e.g. from the European Patent Office laid open print No. 01 42 759 or the European Patent Office laid open print No. 01 90 093. In the case of these known hip cups, the outer cup is structured as a ring, the internal form of which includes at least one conic section. The outer form of the cup body contains a corresponding conic section and is fixed in the outer cup by means of a cone clamping connection. Supported in the cup basin of the cup body, which is exposed on the wide surface of the outer cup, is the his head of the associated hip prosthesis, and because of the considerable stressing of the cup body by the hip head that is moved because of the leg movements, occurring is a cold flow and a subsequent deformation of the plastic cup body. Because of this, the cup body loosens itself, at least partially, from the outer cup, and there occurs the undesired, permanent relative movement between cup body and outer cup, which leads to abrasion of the plastic and to inflammations of the adjoining natural tissue.

Hence, the object of the invention is to develop the hip cup of the initially mentioned species such that the cup body can be firmly fixed, over a large surface, in the outer cup, so that remaining deformations and relative movements of the cup body with movements of the joint are avoided.

This problem is solved in accordance with the invention through the fact that the supporting surface of the cup body is enclosed by a tightly fitting metallic jacket and that the insert formed of the cup body and jacket can be anchored in the outer cup in tightly fitting fashion with at least one attaching element.

The advantages of the invention lie in particular in the fact that the cup body is enclosed in the metallic jacket and, together with the jacket, forms an insert that is supported and anchored in tightly fitting fashion and immovable in the outer cup. The jacket is installed on the cup body by the manufacturer and anchored to the cup body such that undesired relative movements between the plastic cup body and adjoining metal surfaces, and therewith also a deformation of the cup body, are positively avoided. During the operation, the doctor needs only set into the outer cup the insert consisting of the cup body and the jacket, and then to anchor this insert, e.g. by means of a snap ring, in the outer cup. By form-fitting between the cup body and the jacket as well as between jacket and the outer cup, it is assured that the forces introduced from the head of the hip will be conducted over a large surface onto the outer cup and from there into pelvic tissue.

One great advantage of the present invention is represented by the fact that the placement of the cup body into the metal jacket is done by the manufacturer of the hip cup—and not intraoperatively by the doctor—because in so doing, even complicated anchoring mechanisms can be installed safely between both parts which, during the operation, can not be installed by the doctor. Advantageously, for example, the cup body can be firmly screwed in by means of an external threading into the corresponding internal threading of the jacket. Particularly preferred, used are additional clamping elements with which the cup body can be pressed into the jacket while generating a surface pressure, so that relative movements and deformations of the cup body can be positively avoided.

Capable of being used as a clamping element is a threaded ring that can be screwed inside an internal threading of the jacket and, with its turning movement, runs up against the cup surface of the cup body and presses this latter into the pot-shaped jacket such that the supporting surface of the cup body fits tightly against the inner surface of the jacket.

Particularly preferred is that the internal threading of the jacket, into which the cup body is screwed, and the internal threading for the threaded ring that presses the cup body into the jacket, be contrarotating. Radial force components that are unavoidable with the movement-clearance of the hip head in the hip cup will then continually bring about that the one of these two threadings will be more firmly screwed in under the effect of this movement-clearance, while the other threading attempts to loosen. A loosening of the cup body out of the jacket is positively avoided by this.

The outer form of the cup body is fitted to the inner form of the jacket. To achieve a still stronger and more uniform surface pressure between cup body and jacket, particularly preferred is to cool the cup body to a predetermined value prior to emplacement and to place it into the jacket in the cold condition and to clamp it with the threaded ring. Then, with subsequent warming, the cup body expands and raises the contacting pressure.

To be able to emplace the outer cup easily into the acetabulum cavity that has been prepared beforehand by means of a suitable tool, machined centrally at its crown is a compound edge opening. The jacket has at its crown a corresponding compound edge, preferentially an octagon edge, in order to further secure the insert consisting of the cup body and jacket against rotation, and in order, in particular, to be able to emplace the insert in various relative angular positions into the outer cup.

This feature is particularly important for dysplasia cup bodies, the cup basin of which runs against the axis of rotation of the outer cup at a certain angle, with the border (flange, rim) of the cup basin running inclined at the same angle against the peripheral edge of the outer cup. In those cases in which insertion of a dysplasia hip cup is indicated, the doctor, because of the compound edge fitting at the crown of the hip cup, can first emplace the outer in the pelvic bone and next set the insert in the desired angular position into the outer cup and then anchor it there.

The outer cup preferentially projects, at the cup opening, axially out over the peripheral edge of the jacket, and has an internal peripheral groove into which can be placed, by the doctor, a snap ring for anchoring the insert. The snap ring radially projects over the jacket and, preferentially, also the threaded ring and therewith represents a further securing that prevents loosening of the threaded ring and/or of the cup body.

The inner form of the outer cup and the form-fitted outer form of the jacket each have a conic section which, at its wide end, passes over into an open cylinder section. The internal threading for acceptance of the threaded ring is seated in this outer cylinder section, the inner threading for acceptance of the cup body is preferentially constructed in the conic section. The peripheral groove for acceptance of the snap ring is seated in the cylinder section of the outer cup.

Particularly preferred, the jacket has at its crown a flat crown surface that borders on the conic section. The crown surface is constructed as a compound edge which, when emplacing the insert, forms a guide with the compound edge opening of the outer cup and is received by this latter. The cup body then has the outer form of a conic section that fits tightly in the corresponding inner form of the jacket.

By doing this, the conic angle of the jacket, respectively of the inner form of the outer cup is large enough so that the insert can be emplaced clamp-free into the outer cup, i.e. such that a clamping cone action is reliably prevented between outer cup and insert.

The invention makes it possible to use identical or different size inserts for various outer cups. Besides this, in the event of possible re-operations, only the insert of the hip cup needs to be replaced if the outer cup is positively anchored.

According to a particularly preferred form of embodiment of the invention, the attaching element for anchoring the insert in the outer cup is constructed as a retaining ring having an external threading. The outer cup, going out from the peripheral edge, is provided with a corresponding internally lying securing threading that projects over the insert in the direction of the axis of rotation by about the height of the retaining ring. If the retaining ring is screwed into the retaining threading, the retaining ring then finally comes to rest flush against the insert and is firmly screwed against the insert in this position. Preferentially, the retaining ring also includes another internal threading that advantageously runs in contrarotating fashion to the outer threading. The cup body has, at the cylindrical base of the ring groove, an outwardly directed peripheral lip which, in its radial extension, is slightly greater than the thread depth of the internal threading of the retaining ring. If, in the case of this form of embodiment of the invention, the retaining ring is screwed against the insert, the internal threading screws itself over the peripheral lip and presses this latter, with a permanent deformation, into the thread courses. By deformation of this peripheral lip, the retaining ring is secured against loosening. This permanent fixing of the retaining ring is particularly effective if the external threading and the internal threading of the retaining ring are contrarotating, hence if, for example, the external threading runs clockwise and the internal threading counterclockwise. Then, loosening of the retaining ring is possible only in the case of destruction of the counter-thread, formed into the cup body, remaining in the region of the peripheral lip.

Advantageous further developments of the invention are characterized by the features of the subclaims.

Explained in more detail in the following with the aid of the drawing is an example of embodiment of the invention.

SHOWN IN:

FIG. 1 is an exploded representation, in cross section, of an insert consisting of jacket and cup body;

FIG. 2 is a cut through the outer cup into which can be placed the insert according to FIG. 1;

FIG. 3 is a cut through the assembled hip cup;

Figure 4:
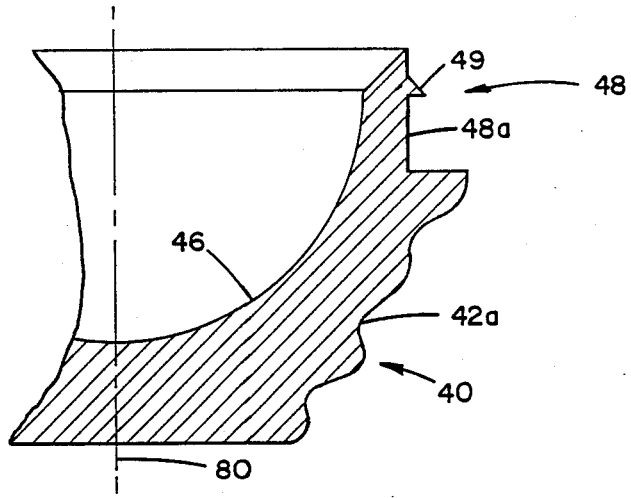
FIG. 4 is a view corresponding to detail A of FIG. 1 of another form of embodiment of the cup body.

FIG. 1 shows an exploded representation of the insert 50 that consists of a jacket 20, a cup body 40 and a threaded ring 72. In the assembled condition, the insert 50 is placed into an outer cup 2, compare FIG. 2, and is anchored there by means of an attaching element, namely a snap ring 62, and therewith forms the hip cup 1, compare FIG. 3. The cup body is a shaped part of plastic into which is formed, on the face side, a somewhat hemispherical-shaped shaped cup surface 46 which, on the face side, runs out into a circular cup edge 47. Adjacent to the cup edge 47 is a ring groove 48 that passes over into a supporting surface 42 that is rotation-symmetric to the axis 80, and forms the outer form of the cup body 40. The supporting surface has the shape of a conic section 42a that is rotation-symmetric to the axis 80, said conic section displaying a flat crown surface. Machined into the supporting surface 42 is an external threading 44.

The jacket 20 consists of metal and has the form of a truncated cone-shaped pot that also has a flat crown surface 32, and encloses in tightly fitting fashion the supporting surface 42 of the cup body 40. Bordering on the wide end of the conic section 22 is an open cylinder section 24 that includes an internal threading 27. The inner surface of the cone section 22 of the jacket 20 has an internal threading 25 into which the external threading 44 of the cup body 40 can be screwed. The screwed-in cup body 40 then lies with its supporting surface 42 closely against the inner surface of the entire jacket 20. Additionally, introduced into the ring groove 48 of the cup body 40 is a threaded ring 72, and fixed in the adjoining internal threading 27 of the jacket 20 such that the threaded ring 72 presses the cup body into the jacket 20 under surface pressure and holds it there and secures it against rotation, because the internal threading 27 is constructed contrarotating to the internal threading 25.

The outer cup 2 that is made of metal has the form of a ring, the inner form of which contains a conic section 12 at whose narrow end is formed, centrally to the ring axis 80, a compound edge opening 10 and whose wide end passes over into a cylinder section 14 that terminates with a face-side peripheral edge 11. Machined in the cylinder section 14—at a predetermined distance from the peripheral edge 11—is a peripheral groove 8. The conic angle of the conic section 12 is identical with the conic angle of the jacket 20. The outer form of the outer cup 2 passes over, from the cylinder section toward the crown, into a conic section 4 that carries an external threading 6 running about the conic axis 80, which is constructed as a cutting thread, and displaying over the entire axial length b of the outer cup an approximately constant external diameter D. The insert 50 is assembled by the manufacturer and, actually, the cup body is screwed to the jacket 20 and then secured with the threading 72 while exerting surface pressure. The insert 50 is placed into the outer cup 2 by the operator during the operation, whereby the compound edge 30 at the crown 32 of the jacket penetrates into the compound opening 10. Next, the insert 50 is secured with a snap ring 62 that is placed into the peripheral groove 8 by the operator, and that projects radially over the jacket 20 and the threaded ring 72.

Figure 5:
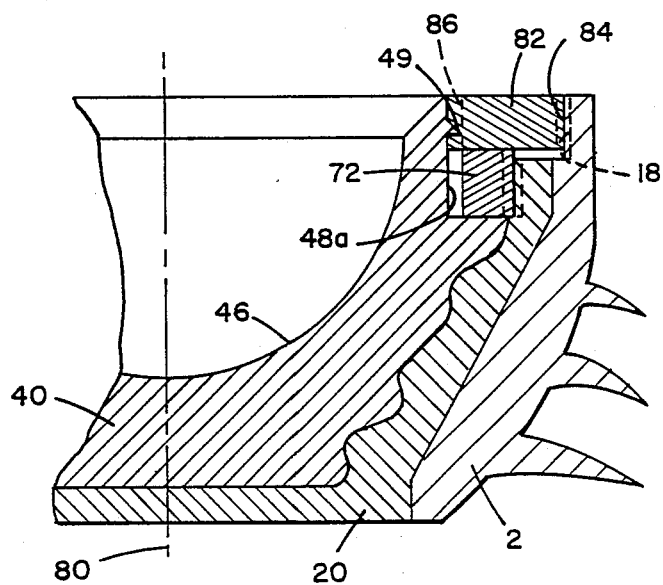
FIG. 5 is an enlarged cut through an assembled hip cup in which is emplaced the cup body according to FIG. 4.

FIG. 4 shows a representation corresponding to detail A of FIG. 1 for a second form of embodiment of the cup body that finds application in a hip cup in accordance with FIG. 5. The basic form of the cup body 40 of FIG. 4 corresponds in all details with the cup body in accordance with FIG. 1. Additionally, however, formed at the cylindrical base 48a of the ring groove 48, at a height that is somewhat greater than the thickness of the threaded ring 72, is a radially outwardly directed peripheral lip 49.

The hip cup in accordance with FIG. 5 is differentiated from the hip cup in accordance with FIG. 3 by the fact that used instead of the snap ring 62 is a retaining ring 82 for anchoring the insert 50 in the outer cup 2. The retaining ring 82 has an external threading 84 that engages into a corresponding retaining threading 18. The retaining threading 18 extends from the peripheral edge 11 on the inner surface of the outer cup 2 in the direction of the axis of rotation 80 up to below the upper edge of the insert 50, and has a larger diameter than the insert 50 at its end facing toward the peripheral edge 11. The retaining ring 82 extends, with its radially enclosed inner surface, up to the cylindrical base 48a of the ring groove 48 of the cup body 40. The retaining ring 82 has on its inner surface an internal threading 86 that is contrarotating to its external threading 84. After the insert 50 is screwed into the outer cup 2, the retaining ring 82 is next screwed into the retaining threading 18 of the outer cup 2 until the underside of the retaining ring 82 lies flush against the threaded ring 72 of the insert 50, and the insert 50 presses firmly into the outer ring 2. When screwing in the retaining ring, its internal threading 86 screws itself over the peripheral lip 49 and presses this latter—with permanent deformation—into the internal threading 86. The height of the retaining ring 82 is dimensioned such that the retaining ring 82, in its screwed-in anchoring position, closes off approximately flush with the peripheral edge 11 of the outer cup 2. In this form of embodiment of the invention, the threaded ring 72 for fixing the cup body 40 in the jacket 20 has an internal diameter that is greater than the external diameter of the ring groove 48, so that the threaded ring 72, when it is being mounted, can be pushed over the peripheral lip 49 without deforming the peripheral lip 49.

What is claimed is:

1. An acetabular prosthesis comprising an outer metallic shell having an outer bone engaging surface and a conically shaped inner surface defining shell cavity;
an insert including, in combination, a metallic jacket, a plastic liner and a threaded ring;
said jacket having an outer surface configured to engage said shell cavity and an inner jacket surface forming a jacket cavity defining a crown end and an opposite open end, and wherein the inner jacket, at a peripheral edge adjacent the open end, has internal threads to mate with aid threaded ring; and
said plastic liner having a part spherical inner liner surface adapted to engage an articulating joint element and an outer liner surface configured to be pressure clamped within the jacket cavity and locked therein upon securing the threaded ring to the internal threads of the jacket, and wherein the insert, in combination, is then fixedly secured within the metallic shell by a retaining means.

2. Hip cup according to claim 1 the outer liner surface being configured to be threadably received in a corresponding threading of the inner jacket surface.

3. Hip cup according to claim 2, characterized by the fact that the internal threading for the cup body and the internal threading for the threaded ring are contrarotating.

4. Hip cup according to claim 1 characterized by the fact that the jacket is closed at the crown and has an outwardly directed compound edge that can be plugged into a corresponding compound edge opening at the crown of the outer cup.

5. Hip cup according to claim 1, characterized by the fact that the retaining means include a snap ring that can be removably installed in the peripheral groove of the outer shell and projects radially over the snap ring.

6. Hip cup according to claim 5, characterized by the fact that the snap ring projects radially over the peripheral edge of the jacket and the threaded ring, between the jacket and the cup body.

7. Hip cup according to claim 1, characterized by the fact that the retaining means include a retaining ring with an external threading, that mates a corresponding threading at the peripheral edge, adjacent the open end of the outer shell, the retaining ring projecting over the insert in the direction of the axis, and being screwed, in the retaining threading, firmly against the insert.

8. Hip cup according to claim 6, characterized by the fact that the retaining ring, when installed, lies flush against the threaded ring.

9. Hip cup according to claim 7, characterized by the fact that the retaining ring displays an internal threading which, when screwing the retaining ring into the outer cup, presses an outwardly directed peripheral lip of the plastic liner with permanent deformation, into the threading.

10. Hip cup according to claim 9, characterized by the fact that the external threading and the internal threading of the retaining ring are contrarotating.

* * * * *

UNITED STATES PATENT AND TRADEMARK OFFICE
CERTIFICATE OF CORRECTION

PATENT NO. : 4,919,674

DATED : 24 April 1990

INVENTOR(S) : Klaus-Dieter Schelhas

It is certified that error appears in the above-identified patent and that said Letters Patent is hereby corrected as shown below:

Front Page,
Item [73]   Assignee:   "Endioprothetick" should be --Endoprothetik--.

Col. 1, line 24, "his" should be --hip--.

Col. 6, line 4, "did" should be --said--

Signed and Sealed this

Eleventh Day of June, 1991

Attest:

HARRY F. MANBECK, JR.

*Attesting Officer*   Commissioner of Patents and Trademarks